US008980595B2

(12) United States Patent  
Ropars et al.

(10) Patent No.: US 8,980,595 B2
(45) Date of Patent: Mar. 17, 2015

(54) IN SITU PRODUCTION OF FURFURAL IN A CONTROLLED AMOUNT IN AN ALCOHOL PRODUCTION UNIT FROM A LIGNOCELLULOSIC BIOMASS

(75) Inventors: Marcel Ropars, Palaiseau (FR); Caroline Aymard, Lyons (FR); Flora Ghisoni, Saint Jeannet (FR); Sandra Menir, Gonesse (FR)

(73) Assignee: IFP Energies Nouvelles, Rueil-Malmaison Cedex (FR)

( * ) Notice: Subject to any disclaimer, the term of this patent is extended or adjusted under 35 U.S.C. 154(b) by 340 days.

(21) Appl. No.: 13/320,323

(22) PCT Filed: May 7, 2010

(86) PCT No.: PCT/FR2010/000351
§ 371 (c)(1),
(2), (4) Date: Jan. 27, 2012

(87) PCT Pub. No.: WO2010/130889
PCT Pub. Date: Nov. 18, 2010

(65) Prior Publication Data
US 2012/0122170 A1    May 17, 2012

(30) Foreign Application Priority Data
May 15, 2009  (FR) ...................... 09 02348

(51) Int. Cl.
C12P 7/02    (2006.01)
C12P 7/16    (2006.01)
(Continued)

(52) U.S. Cl.
CPC . *C12P 7/10* (2013.01); *C12P 17/04* (2013.01); *Y02E 50/16* (2013.01); *C12P 2201/00* (2013.01)
USPC .............................. 435/155; 435/160; 435/41

(58) Field of Classification Search
None
See application file for complete search history.

(56) References Cited

U.S. PATENT DOCUMENTS

2011/0053238 A1    3/2011    Ohgren Gredegard et al.

FOREIGN PATENT DOCUMENTS

WO    2009/102256 A2    8/2009

OTHER PUBLICATIONS

Oh, Kyeong Keun, et al., "Pretreatment of Lignocellulosic Biomass using Combination of Ammonia Recycled Percolation and Dilute-Acid Process," Journal of Industrial and Engineering Chemistry, Jan. 2002, vol. 8, No. 1, pp. 64-70; cited in International Search Report, dated Dec. 27, 2010, issued in corresponding PCT/FR2010/000351.

(Continued)

*Primary Examiner* — Alexander Kim
(74) *Attorney, Agent, or Firm* — Millen, White, Zelano & Branigan, P.C.

(57) ABSTRACT

The present invention describes a process for the production of alcohol, known as second generation production, from a lignocellulosic substrate, in which a controlled quantity of furfural is produced in situ and which comprises at least the following steps:
   a first step for alkaline chemical pre-treatment of the substrate;
   a step for adjusting the pH of the substrate; then
   a step for enzymatic hydrolysis of said pre-treated substrate;
   a step for alcoholic fermentation of the hydrolysate obtained with an alcohol-producing microorganism;
   a step for separation/purification; and
   a step for acid conversion of at least one liquid fraction into furfural, said liquid fraction being obtained during one of the preceding steps;
   a step for mixing said furfural obtained with the pre-treated substrate during the pH adjusting step.

20 Claims, 2 Drawing Sheets

(51) Int. Cl.
*C12P 1/00* (2006.01)
*C12P 7/10* (2006.01)
*C12P 17/04* (2006.01)

(56) References Cited

OTHER PUBLICATIONS

Larsson, S. et al., "The generation of fermentation inhibitors during dilute acid hydrolysis of softwood," Enzyme and Microbial Technology, Jan. 1, 1999, vol. 24, pp. 151-159, Elsevier Science Inc., New York, NY; cited in International Search Report, dated Dec. 27, 2010, issued in corresponding PCT/FR2010/000351.

Ohgren, K., et al., "Simultaneous saccharification and co-fermentation of glucose and xylose in steam-pretreated corn stover at high fiber content with *Saccharomyces cerevisiae* TMB3400," Journal of Biotechnology, Dec. 1, 2006, vol. 126, No. 4, pp. 488-498, Elsevier Science Publishers, Amsterdam, NL; cited in International Search Report, dated Dec. 27, 2010, issued in corresponding PCT/FR2010/000351.

Carvalheiro, F., et al., "Hemicellulose biorefineries: a review on biomass pretreatments," Journal of Scientific and Industrial Research, Nov. 2008, vol. 67, No. 11, pp. 849-864, cited in International Search Report, dated Dec. 27, 2010, issued in corresponding PCT/FR2010/000351.

International Search Report, dated Dec. 27, 2010, issued in corresponding PCT/FR2010/000351.

Written Opinion, dated Dec. 27, 2010, issued in corresponding PCT/FR2010/000351.

FIGURE 1

IN SITU PRODUCTION OF FURFURAL IN A CONTROLLED AMOUNT IN AN ALCOHOL PRODUCTION UNIT FROM A LIGNOCELLULOSIC BIOMASS

FIELD OF THE INVENTION

The context of the present invention is in so-called "second generation" processes for the production of alcohol from lignocellulosic biomass.

STUDY OF THE PRIOR ART

Lignocellulosic biomass represents one of the most abundant renewable sources on the planet, and certainly one of the cheapest. The substrates under consideration are highly varied since they concern both ligneous substrates (deciduous and coniferous), agricultural by-products (straw) or those from industries generating lignocellulosic waste (agroalimentary or paper industries).

Lignocellulosic biomass is composed of three principal polymers: cellulose (35% to 50%), hemicellulose (20% to 30%), which is a polysaccharide essentially constituted by pentoses and hexoses, and lignin (15% to 25%), which is a polymer with a complex structure and a high molecular weight originating from the co-polymerization of phenylpropenoic alcohols. Those various molecules are responsible for the intrinsic properties of the plant wall and are organized into a complex network.

Cellulose and possibly hemicelluloses are the targets for enzymatic hydrolysis, but they are not directly accessible to enzymes. For this reason, such substrates have to undergo a pre-treatment preceding the enzymatic hydrolysis step. The pre-treatment is intended to modify the physical and physico-chemical properties of the lignocellulosic material with a view to improving the accessibility of the cellulose inserted into the matrix of lignin and hemicellulose.

Many techniques for carrying out such a pre-treatment exist: acid digestion, alkaline digestion, steam explosion, organosolve processes, etc. The efficiency of the pre-treatment is measured both by the material balance at the end of the pre-treatment (recovery yield for sugars in the form of soluble monomers or oligomers or solid polymers) and also by the susceptibility of the cellulosic and hemicellulosic residues to hydrolysis.

Acid pre-treatment under mild conditions and by steam explosion is very often employed, since recovery of the pentoses is high (more than 90%) and accessibility to the cellulose on enzymatic hydrolysis is good. It can in fact liberate the sugars contained in the hemicelluloses in the form of monomers, essentially pentoses such as xylose and arabinose, and hexoses such as galactose, mannose and glucose. That type of pre-treatment also generates sugar degradation products which are principally aldehydes such as furfural or 5-HMF (hydroxymethyl furfural). Those two products respectively originate from the degradation of pentoses or hexoses in an acid medium and at high temperature. Many other products such as organic acids, aldehydes or phenolic alcohols are also derived from the acid degradation of sugars and partially dissolved lignin.

Those products, in particular furfural, which latter corresponds to the degradation product which usually has the highest concentration, are toxic to all microorganisms and thus to the yeast which is to transform the sugars into alcohol by fermentation. Such toxic compounds are termed "inhibitors" and originate from a pre-treatment carried out under hot acidic conditions. An example that can be cited is Klinke H B, Schmidt A S, Thomsen A B (1998), Biomass for Energy and Industry, Proceedings of the 10$^{th}$ European Conference and Technology Exhibition, CARMEN, Rimpar, Germany, 484-487, or Palmquist et al, (2000), Biores Technol 74: 1, 17-24. After that type of pre-treatment, the concentrations may be in the range 3 to 5 g/L of furfural and 1 to 5 g/L of 5-HMF and are not checked. The presence of 5-HMF and furfural associated with phenolic alcohols and aldehydes causes major problems with toxicity. Several teams are currently working on detoxification methods which could facilitate sugar fermentation, more particularly by yeasts or alcohol-producing bacteria. An example that may be cited is the article by Canterella et al published in Process Biochemistry (2004), vol 39, issue 11, pp 1533-1542.

The sugars obtained by hydrolysis of the lignocellulosic biomass are pentoses (principally xylose and arabinose) and hexoses. Glucose is the principal available sugar. It is readily transformed into ethanol by the yeast S. cerevisiae used by all alcohol fermentation industries. In contrast, pentoses are only fermented by specific yeasts (P. stipitis, P. tannophilus) and the performance is mediocre.

Alcoholic fermentation under non-sterile conditions suffers from the major risk of contamination of the fermenter by opportunistic microorganisms. Those microorganisms use nutrients present in the medium and may be responsible for the formation of unwanted co-products such as lactic acid or acetic acid. That type of microorganism is found anywhere that conditions allow them to grow, i.e. in the presence of a minimum of nutrients. It should be mentioned here that their nutritional demands are as follows: a source of carbon (generally sugars), a source of amino acids (constituents of proteins), certain vitamins and oligo-elements.

Bacterial contamination is a major problem in the production of alcohol by fermentation. The bacteria naturally present in the production tool use nutrients present in the medium and compete with the yeasts used in the process. The growth and viability of the yeast cells are thus strongly affected by the presence of said bacteria and the final alcohol yield therefrom is also reduced.

Lactic bacteria are included as potential contaminants. In general, they ferment sugars present in fermentation mash and their growth is promoted by anaerobic conditions. They generally develop at a pH of 5.5, but can survive at a pH as low as 3.0. Such opportunistic bacteria may develop over a wide temperature range and are tolerant to high concentrations of alcohol in the medium. The presence of bacteria in second generation alcohol production processes must be prohibited.

Thus, in the current non-sterile second generation process for the production of ethanol, two steps are sensitive to possible microbiological contamination: the enzymatic hydrolysis step, most particularly, and the fermentation step. Current solutions for combating lactic contamination during the fermentation step consist, for example, of reducing the pH to a value that promotes the development of yeasts to the detriment of lactic bacteria. However, yeasts are less active at these acidic pHs. That type of solution is not possible, however, for the enzymatic hydrolysis step. Another combatting possibility consists of introducing bacterial contamination inhibitors such as fluorides, antibiotics or sulphites. Those procedures are applied in first generation processes for the production of ethanol. Using conventional antibacterials is relatively expensive and boosters have to be added fairly frequently to re-launch the fermentation process.

In contrast to the acid pre-treatments described in the prior art, the alkaline pre-treatment of the present invention does not generate any of the sugar degradation products usually obtained in acid pre-treatments. Thus, that type of pre-treatment does not induce the production of furfural. For this reason, a hydrolysate from a plant prepared under alkaline conditions would be sensitive to bacterial infections both in the enzymatic hydrolysis step and in the fermentation step. This problem is also encountered in a process that simultaneously combines the two steps of enzymatic hydrolysis and alcoholic fermentation (the SSF process, simultaneous saccharification and fermentation).

Limiting contamination risks constitutes a big potential saving in time and money for scaled-up industrial processes and no solution to this problem should be ignored. Any improvement in the process resulting in limiting this contamination as much as possible should be taken into consideration. The present invention falls into this category and proposes a process for the production of alcohol with alkaline pre-treatment and anti-bacterial protection.

SUMMARY OF THE INVENTION

The present invention describes a so-called "second generation" process for the production of alcohol from a lignocellulosic biomass using an alkaline pre-treatment and in which an anti-bacterial agent (furfural) is produced in situ in a controlled dose by the acid conversion of pentoses derived directly from the process in order to protect the sugars present in the enzymatic hydrolysis and/or fermentation step.

DETAILED DESCRIPTION OF THE INVENTION

The process for the production of alcohol from a cellulosic or lignocellulosic substrate is a process in which furfural is produced and which comprises at least the following steps:
  a first step for alkaline chemical pre-treatment (step A) of said substrate, comprising a step A1 for heating in the presence of an alkaline chemical reagent, at the end of which at least one stream comprising at least said chemical reagent and the pre-treated substrate are obtained, and optionally a step A2 for washing said pre-treated substrate, at the end of which the pre-treated washed substrate and at least one stream containing spent washing water are obtained; then
  a step for bringing the pre-treated and optionally washed substrate to a pH in the range 4.5 to 5.5, coupled with a step for enzymatic hydrolysis (step B1) of said pre-treated substrate using cellulolytic and/or hemicelluloytic enzymes;
  a step (step B2) for alcoholic fermentation of the hydrolysate obtained with an alcohol-producing microorganism, at the end of which a fermentation mash is obtained comprising material in suspension and a liquid phase comprising an alcohol and vinasses; then
  a step (step C) for separation/purification, at the end of which purified alcohol, clarified vinasses and an insoluble residue are obtained; and
  a step (step D) for acid conversion of at least one of the liquids obtained during one of the preceding steps and containing dissolved pentoses, a portion of said pentoses being converted into furfural; and
  a step for mixing furfural obtained during the acid conversion step with the pre-treated substrate optionally washed during the pH adjusting step, the quantity of furfural mixed in being in the range 1 to 5 g/L with respect to the total quantity of liquid employed in the enzymatic hydrolysis step and/or the alcoholic fermentation step.

In the context of the present invention, the term "pentose" is used to denote soluble monomers and oligomers of sugars containing 5 carbon atoms.

The process of the present invention thus proposes to upgrade pentoses by transforming these compounds into furfural. As a result, the process of the present invention proposes the in situ production of a controlled quantity of an anti-bacterial agent intended to protect the various sugars present in the enzymatic hydrolysis and alcoholic fermentation step.

This process also has the advantage of improving the yield for conversion of C6 sugars into alcohol, by limiting the production of glycerol, which is the principal by-product in alcoholic fermentation.

Further, mixing an acid solution comprising furfural produced by the conversion of pentoses with the pre-treated substrate can highly advantageously be used to participate in the necessary pH adjustment of the pre-treated substrate before carrying out the enzymatic hydrolysis.

The alkaline chemical pre-treatment carried out in step A is preferably a Kraft type pre-treatment at the end of which paper pulp is obtained.

The sodium sulphate or Kraft process is based on the use of sodium hydroxide and sodium sulphate. The chemical treatment of wood chips is carried out at 150-175° C. for a period of 1 to 7 hours depending on the substrate used. This Kraft paper pulp is produced from a very broad range of biomasses, but more particularly from coniferous arborescent species (softwoods such as spruce or pine) or deciduous species (hardwoods such as eucalyptus) or from agricultural lignocellulosic waste (straw from wheat, rice etc). They are partially delignified by cooking at high temperature in the presence of sodium hydroxide. This delignification is controlled by the operating parameters of the reactors. The cooking is carried out in a vertical reactor where the chips descend under gravity and encounter the various liquors from cooking. The sodium sulphide is prepared directly from sodium sulphate by combustion. During cooking, the sodium sulphide is hydrolyzed into sodium hydroxide, NaHS and $H_2S$. The various sulphur-containing compounds present react with the lignin to produce more readily soluble thiolignins. The liquor applied to the chips is termed white liquor. The liquor extracted from the reactor or digester containing the compounds eliminated from the wall is termed black liquor.

Following this alkaline pre-treatment, a pre-treated substrate is produced which is enriched in cellulose since it contains in the range 60% to 90% of cellulose and in the range 5% to 20% of hemicellulose. This substrate is then partially washed.

Other alkaline pre-treatments have been studied on a laboratory scale with the aim of reducing the costs of this step when producing a fuel.

The alkaline chemical pre-treatment carried out in step A may also be an ammonia fiber explosion pre-treatment, also termed AFEX pre-treatment, or an ammonia recycle percolation pre-treatment, also termed ARP pre-treatment.

The ARP (ammonia recycle percolation) process is a pre-treatment process using ammonia in recycle mode. This type of process has in particular been described by Kim et al, 2003, Biores Technol 90 (2003), pp 39-47. The high temperature of the percolation results in partial dissolution of both the lignin and the hemicelluloses, then this solution is heated to recycle the ammonia and to recover the extracted lignin, for example for energy recovery, and also the soluble sugars derived from the hemicelluloses.

The AFEX (ammonia fiber explosion) process consists of introducing the lignocellulosic substrate into a high pressure digester in the presence of ammonia then causing an explosive decompression at the reactor outlet and then recycling the ammonia which is then in the gaseous form. This type of process has been described in particular by Teymouri et al, 2005, Biores Technol 96 (2005), pp 2014-2018. This process principally results in destructuring the biomass matrix, but there is no phase separation of the lignin, hemicellulose and cellulose compounds at the outlet from the treatment.

Other alkaline treatments are also being studied, in particular based on sodium hydroxide or lime; a non-exhaustive review has been provided by Ogier et al, 1999, Oil & Gas Science and Technology, IFP review, Vol 54 (1999), No 1, pp 67-94.

These alkaline pre-treatments may be combined with a mechanical action created, for example, in a twin screw extruder or a pulper.

Optional step A2 is a step consisting of washing the pre-treated substrate by introducing one or more wash liquids. This washing step may also be limited to a dilution step.

The pre-treated substrate obtained, which may have been washed, includes insoluble solid materials and possibly a liquid fraction.

The pH of the substrate from the pre-treatment has to be adjusted in order to carry out the enzymatic hydrolysis step. Enzymatic hydrolysis is carried out under mild conditions, at a temperature of the order of 45-50° C. and a pH in the range 4.5 to 5.5. Most preferably, the pH is in the range 4.8-5.2. This pH adjustment may be carried out separately or at the entrance to the enzymatic hydrolysis reactor. Advantageously, the pH adjustment is carried out by mixing the product obtained after the acid conversion step with the stream comprising the pre-treated substrate, optionally supplemented, if necessary, by adding an acid solution.

Because of the alkaline pre-treatment, accessibility of the cellulose and the hemicelluloses is improved and their susceptibility to enzymatic hydrolysis is excellent. During this saccharification step, the cellulose and hemicellulose polymers are converted into "highly fermentable (glucose, mannose), "poorly fermentable" (galactose) and "hardly fermentable" (xylose and arabinose) sugars.

The enzymatic hydrolysis (step B1) is carried out using enzymes produced by a microorganism. Microorganisms such as fungi belonging to the genuses *Trichoderma, Aspergillus, Penicillium* or *Schizophyllum,* or anaerobic bacteria belonging, for example, to the genus *Clostridium,* produce these enzymes, in particular containing cellulases and hemicellulases, which are adapted to the intense hydrolysis of cellulose and hemicelluloses.

Step B2 is the alcoholic fermentation step: the fermentable sugars are thus transformed into alcohols by the yeasts. Fermentation is usually carried out at a temperature in the range 30° C. to 35° C. At the end of this step, a fermentation mash is obtained comprising material in suspension and a liquid phase which contains the alcohol produced.

When steps B1 and B2 are carried out simultaneously in the same reactor, this constitutes the SSF process. The temperature is then about 35° C.

When enzymatic hydrolysis of the sugar polymers and fermentation of the glucose and xylose are carried out simultaneously, this constitutes the SSCF (simultaneous saccharification and co-fermentation) process. The temperature is then about 35° C.

Step C is the step for separation/purification of the product which can produce a purified alcohol that is ready for sale. This step advantageously comprises three sub-steps: a distillation step to obtain an alcohol as an azeotrope, a dehydration step to produce the dehydrated alcohol ready for use as a fuel, and a step for clarification of the vinasses to separate the insoluble residues from the waste water.

Depending on the quantity of solid residue, the separation step is carried out before or after the distillation step.

Step D corresponds to the acid conversion step and thus to the manufacture proper of the anti-bacterial agent.

The acid conversion (step D) is carried out at a temperature in the range 120° C. to 200° C. for a period of 0.5 to 3 hours, in the presence of a strong acid, preferably selected from sulphuric or phosphoric acid.

Preferably, the acid conversion is carried out at a temperature in the range 130° C. to 190° C. for a period of at most 1.5 hours, in the presence of a 1% to 8% sulphuric acid solution.

In accordance with one implementation of the process of the invention, liquid containing the dissolved pentoses used during the acid conversion step is a liquid fraction of the clarified vinasses stream obtained at the end of the separation/purification step (step C).

The liquid fraction employed in the acid conversion step represents in the range 5% to 75% by weight, preferably in the range 10% to 60% by weight, of the stream of clarified vinasses.

In accordance with another implementation of the process of the invention, the liquid containing the dissolved pentoses used during the acid conversion step is a fraction of the stream containing at least the chemical reagent and the pre-treated substrate, obtained after the pre-treatment step.

This liquid fraction represents 10% to 100% by weight of said stream, preferably in the range 20% to 100% by weight.

In accordance with another implementation of the process of the invention, the liquid containing the dissolved pentoses used in the acid conversion step is a fraction of the stream containing the spent washing water obtained after the pre-treatment step. This liquid fraction represents 10% to 100% by weight, preferably in the range 20% to 100% by weight of said stream.

All of the product resulting from the acid attack carried out in step D is mixed with the pre-treated substrate stream, optionally washed, during the pH adjustment necessary for the enzymatic hydrolysis step.

The presence of furfural in controlled concentrations, for example in the range 1 to 5 g/L, can considerably reduce the development of bacterial contaminants, in particular lactic bacteria. At these same concentrations of furfural, the alcohol-producing yeast is only slightly affected. The concentrations of furfural are given with respect to the fraction of liquid entering the enzymatic hydrolysis and/or fermentation reactors.

The acceptable concentration of furfural for which the anti-bacterial agent function of the furfural is fulfilled without it becoming a toxic product for the yeast is dependent on the operating conditions of the process and the yeast used.

In the process of the invention, the step for acid attack of the pentoses essentially produces furfural. Thus, this latter constitutes the inhibitor compound which is primarily present, optionally associated with traces (less than 0.1 g/L) of acetic and formic acid. By way of comparison, it will be recalled that in pre-treatment processes carried out under acid conditions (such as steam explosion or acid digestion), furfural is only one of the inhibitor compounds among about fifty identifiable products obtained. In those processes, it thus becomes very difficult to properly manage the antimicrobial action which is the result of isolated or synergistic effects of compounds derived from the degradation of sugars or lignin.

A concentration of furfural obtained under the conditions of the process of the present invention thus means that the bacterial populations can be controlled.

Initially, the concentration of 1 g/L of furfural is sufficient since the bacteria are not adapted to this product. However, it rapidly becomes necessary to increase the concentration of furfural well above 1 g/L to reduce bacterial infection, in particular that from lactic bacteria. It is not recommended to exceed a concentration of 5 g/L as it would start to have a deleterious effect on the fermentation performances of yeasts of the genus saccharomyces (reduction in productivity). This adjustment in the concentration is in particular possible by monitoring and adjusting the streams which are sent to the acid conversion step.

Next, the presence of a controlled quantity of furfural in the process of the invention means that the production of glycerol, the principal co-product of alcoholic fermentation and responsible for the reduction in the conversion yield for C6 sugars (glucose and hexoses) into alcohol, can be reduced. Adding furfural to the medium obliges the yeast used during the alcoholic fermentation step to reduce it to furfuryl acid by means of co-factors (NADH). This reduction is prioritized over the formation of glycerol which conventionally may be responsible for a loss of 5% to 8% of carbon. In a medium containing no furfural, the indispensible regeneration of co-factor is carried out by the synthesis of glycerol from glucose, thus affecting the yield of alcohol production.

The furfural constitutes a protection against bacterial contaminants and in particular lactic contaminants, at temperatures of 30° C. to 70° C., which corresponds to the temperatures at which enzymatic hydrolysis (40-50° C.) and alcoholic fermentation (30-35° C.) are carried out.

The process for the production of alcohol from lignocellulosic biomass will now be described with reference to the figures.

DETAILED DESCRIPTION OF THE DRAWINGS

Figure 1:
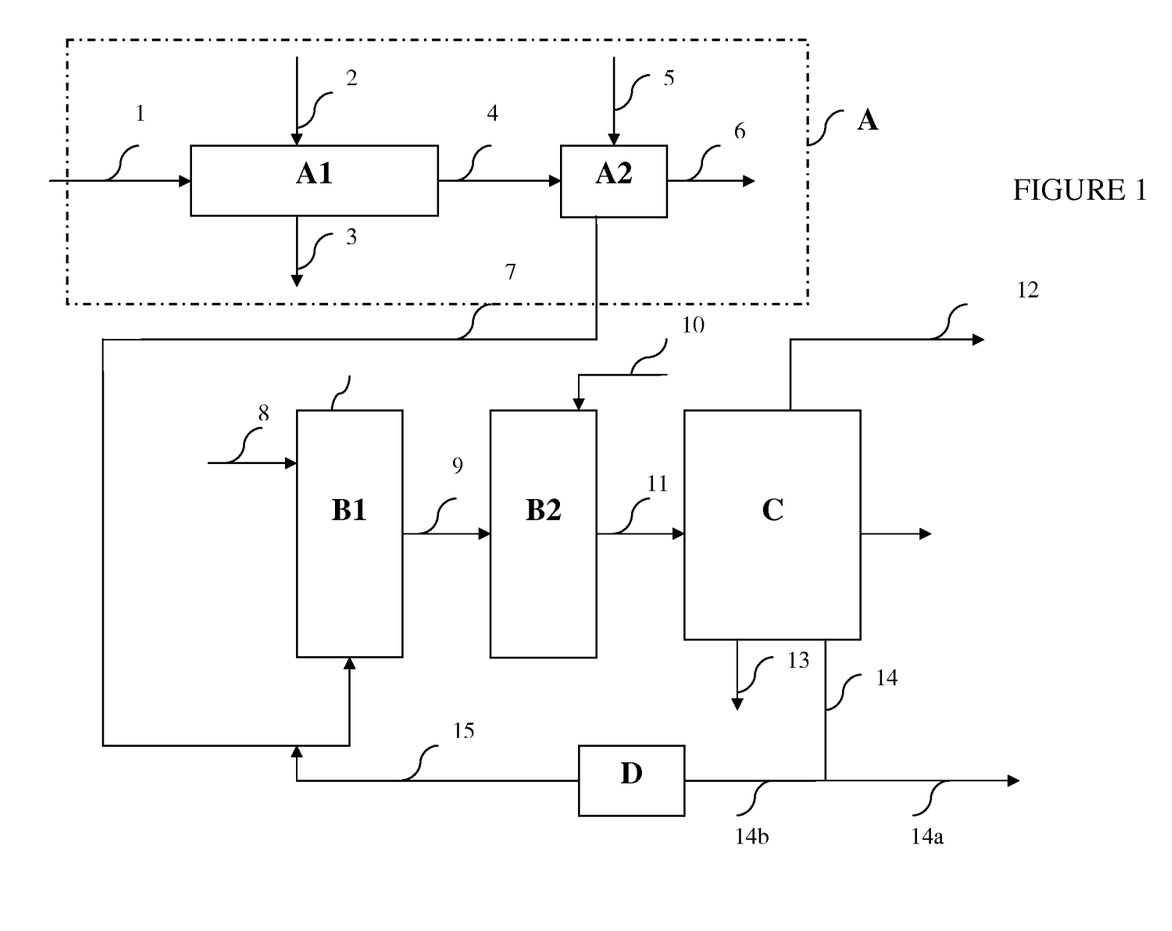
FIG. 1 shows a layout of the process of the invention in a first implementation in which the liquid fraction comprising the pentoses, which undergoes the acid conversion, derive from clarified vinasses.
Figure 2:
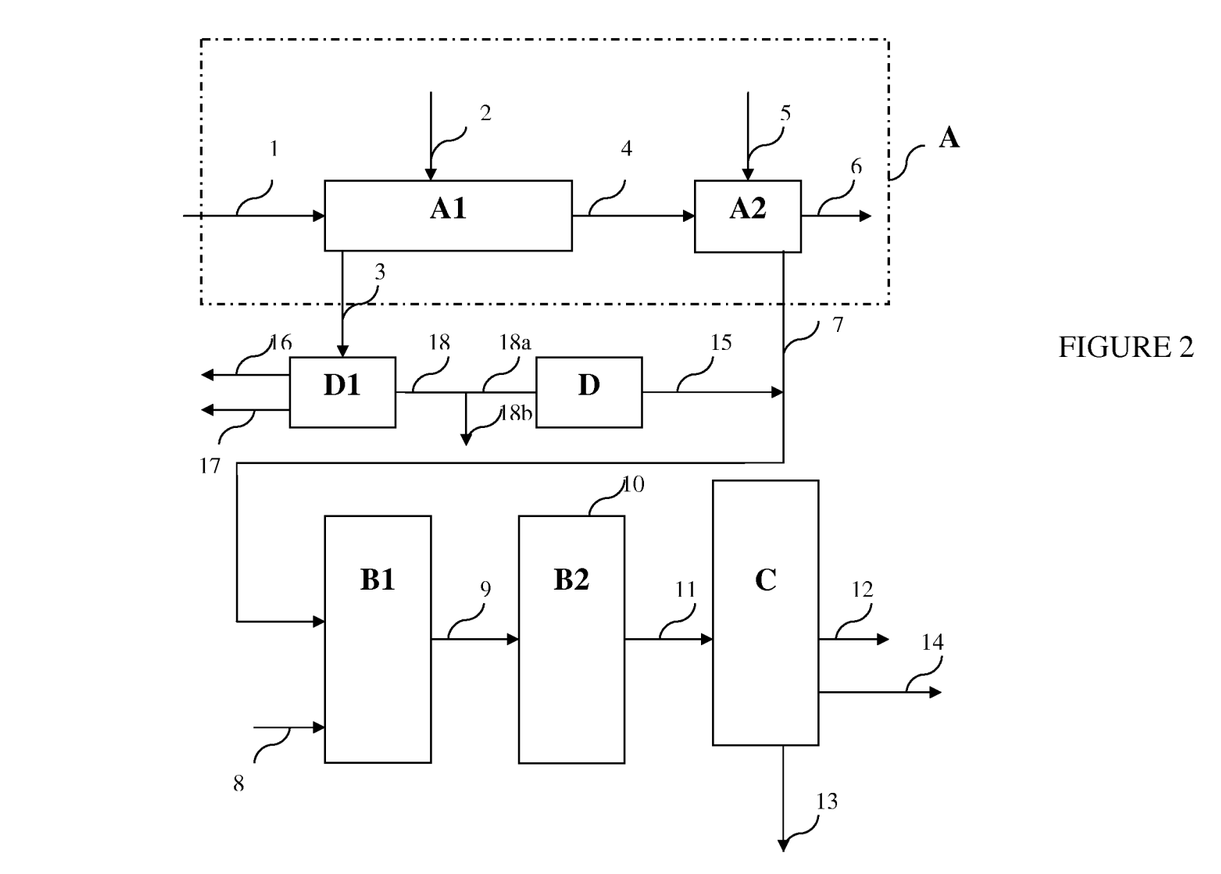
FIG. 2 shows a layout of the process of the invention in a second implementation in which the liquid fraction comprising the pentoses, which undergoes the acid conversion, are derived from the spent alkaline solution obtained at the outlet from the pre-treatment after separation.

Stations A to D shown in the figures respectively correspond to the various steps of the process of the present invention, designated by identical letters.

The function of station A is particularly dependent on the pre-treatment under consideration.

In the case of a pre-treatment known as Kraft pre-treatment, the biomass is introduced via a line 1 into the cooking reactor or digester (A1). An alkaline solution, also termed white liquor, is also introduced into it via the line 2. The biomass is partially delignified by cooking at high temperature and in the presence of sodium hydroxide. The dissolved lignin is removed with the alkaline solution and is evacuated via the line 3 with the spent alkaline solution, also termed black liquor.

This delignification step may be carried out in several successive digesters, not shown in the figures, and is controlled by the operating parameters set for these devices.

The pulp obtained from the outlet from the digesters moves in the line 4; it corresponds to the pre-treated substrate and is enriched in cellulose: it contains in the range 60% to 90% by weight of cellulose with respect to the total solid material. It is sent to the reactor A2 to undergo a washing step: one or more washing liquids may be introduced via a line 5. This washing step is followed by a step for adjusting the pH of the pulp for the enzymatic hydrolysis step (step B). The spent washing liquids are withdrawn via the line 6.

In the case of an AFEX treatment, the biomass is introduced via the line 1 into a cooking reactor (A1). An ammoniacal solution is introduced via the line 2 at a pressure of 15 to 30 bars, at a moderate temperature (70° C. to 110° C.). The mixture is held under these conditions for a predetermined time as a function of the substrate, then is depressurized at the digester outlet. The ammoniacal solution is recovered via the line 3 in the form of a gas for recycling. The pre-treated substrate extracted via the line 4 of the digester essentially has the same composition as the inlet substrate. The washing step A2 after this pre-treatment may be limited to a dilution step with a diluting liquid being introduced via the line 5, in which case the stream of washing liquid evacuated via the line 6 is zero. The pH adjustment step can then be carried out to adapt it to enzymatic hydrolysis.

In the case of an ARP pre-treatment, the biomass is introduced via the line 1 into the cooking reactor (A1). An ammoniacal solution is percolated over the biomass under pressure (15 to 30 bar) and at high temperature, 130° C. to 190° C. The biomass is partially delignified, a portion of the hemicelluloses is also dissolved. The sugars and the dissolved lignin are withdrawn with the spent alkaline solution and are evacuated via the line 3. The pre-treated substrate from cooking extracted via the line 4 is washed in a washing reactor (A2): one or more washing liquids may be introduced via the line 5. Said washing step is followed by a step for adjusting the pH of the substrate to adapt it to enzymatic hydrolysis. The spent washing liquids are removed via the line 6.

At the end of the pre-treatment, the substrate moving in the line 7 contains between 1% and 55% by weight, preferably between 1% and 45% by weight, of insoluble solid material and is sent to the alcohol conversion steps, comprising at least one step for enzymatic hydrolysis (step B1) and at least one step for alcoholic fermentation (step B2).

In the enzymatic hydrolysis step B1, an enzymatic solution containing cellulolytic and/or hemicelluloytic enzymes is introduced via the line 8 and mixed with the pre-treated substrate, optionally washed, moving in the line 7.

The hydrolysate obtained at the end of step B1 evacuated via the line 9 is constituted by pentoses (principally xylose and arabinose), disaccharides (cellobiose) and hexoses (galactose, mannose and especially glucose). It is then sent to the station B2 where alcoholic fermentation takes place in the presence of yeasts or other microorganisms introduced via the line 10.

The fraction obtained after fermentation is sent via the line 11 to the station C where the separation/purification step takes place. The solid residues, the alcohol produced and the clarified vinasses are separated out.

In the implementation represented in FIG. 1, at the end of step C for separation/purification, all of the hexoses (glucose and mannose) which were present in the stream leaving the enzymatic hydrolysis have been converted into alcohol and are extracted via the line 12. The pentoses are not used as they fall into the "difficult to ferment" sugar category and are found in the clarified vinasses extracted via the line 14, for example at the foot of the distillation column. The principal pentose present in the vinasses is xylose. As an example, for a 100 g/L mash of glucose, and depending on the plant source, the concentration of xylose may be in the range 5 to 55 g/L.

The stream of clarified vinasses is then separated into two streams moving respectively in lines 14a and 14b. A portion of the stream representing in the range 5% to 75% by weight of the total vinasses is directed into the line 14b towards an acid conversion reactor (station D). By heating, a fraction of the pentoses contained in this stream which depends on the selected operating conditions is then specifically converted into furfural. The stream of the product obtained after the acid attack is evacuated via the line 15.

As an example, if the acid cook is relatively moderate, (120° C., 1.5 hours, 4% sulphuric acid), close to 20% of the pentoses may be converted into furfural without the furfural itself being degraded into by-products. At most 2% to 3% of the furfural may be converted into formic acid and/or furfural polymer.

The product obtained from the acid attack moving in the line 15 and comprising furfural is then advantageously mixed with the stream moving in the line 7 constituted by the pre-treated plant material before being sent to the enzymatic hydrolysis step.

The other portion of the stream of vinasses is extracted via the line 14a for treatment to upgrade the pentoses.

The alcohol produced is extracted via the line 12 and the solid residues obtained after the separation/purification step (step C) are evacuated via the line 13.

The implementation shown in FIG. 2 more particularly corresponds to an implementation of the process of the present invention in which the pre-treatment carried out is an ARP type pre-treatment with which a step for regenerating the ammoniacal solution is associated.

The biomass is introduced via the line 1 into a cooking reactor (A1). An ammoniacal solution is percolated over the biomass under pressure (15 to 30 bars) and at high temperature, 130° C. to 190° C. The biomass is partially delignified; a portion of the hemicelluloses is also dissolved. The sugars and the dissolved lignin are withdrawn with the spent alkaline solution and are evacuated via the line 3. A step (D1) for regeneration of the ammoniacal solution may be added, which means that at least two streams, preferably at least three streams, can be generated: a first stream moving in the line 18 constituted by all or a portion of the dissolved sugars in solution, and a second stream moving in the line 16 containing the alkaline solution. The lignin may be contained in the second stream moving in the line 16 or, preferably, in a separate stream evacuated via a line 17. In the case of an ARP type pre-treatment, this regeneration is evaporation of the ammoniacal solution.

The sugars derived from the hemicelluloses are recovered in a stream moving in the line 18. This stream contains soluble materials which are principally pentoses and hexoses derived from the hemicelluloses, and, in smaller quantities, the organic acids derived from the partial degradation of lignin.

In certain cases, depending on the composition of the hemicelluloses of the initial substrate, the proportion of hexoses in the stream from the line 18 may represent up to 70% of the dissolved sugars. However, the implementation of FIG. 2 is preferably used for substrates for which the proportion of hexoses in the hemicelluloses is less than 20%, more preferably less than 10% of the hemicelluloses.

In a variation of the implementation corresponding to FIG. 2, not shown, the station D1 for separating sugars from the alkaline solution may be placed on the stream for the liquids for washing the pre-treated substrate moving in the line 6.

A portion representing 5% to 100% by weight of the stream moving in the line 18 (stream 18a) is directed to an acid conversion reactor. On heating, a fraction of the pentoses is thus specifically converted into furfural. The stream of product from the acid attack is evacuated via the line 15. Under the acid heating conditions described above, the product from the reaction is essentially furfural. However, it is not excluded that small quantities of 5-HMF and levulinic and formic acid from the degradation of traces of hexoses can be obtained.

The fraction 18b which is not sent to the acid conversion reactor is treated in order to upgrade these sugars.

The stream leaving the acid conversion reactor via the line 15 may then be mixed with the stream 7 leaving the pre-treatment step and intended to be sent to the enzymatic hydrolysis reactor (step B1).

Thus, the stream of acid solution comprising the antimicrobial agent also contributes to the pH adjustment of the stream from the alkaline chemical pre-treatment prior to the enzymatic hydrolysis step.

The examples below illustrate the invention without limiting its scope.

EXAMPLE 1

A process for the production of ethanol from "Kraft" type paper pulp is considered. The pulp was obtained from softwood pre-treated in a Kraft type papermaking process, which is an alkaline process carried out in the presence of sodium hydroxide. The lignin-depleted pulp from the Kraft process is then washed and neutralized, then introduced into the process for the conversion of cellulosic substrate to ethanol by enzymatic hydrolysis and fermentation of glucose and mannose (sugars containing 6 carbon atoms).

The process treated 40 tonnes/hour of pulp (based on dry matter). The composition of the dry matter was as follows:

| | |
|---|---|
| Cellulose (%) | 77.75% |
| Xylanes (%) | 8.96% |
| Mannanes (%) | 5.26% |
| Others (%) | 7.68% |

The process for conversion to ethanol contained the following steps: enzymatic hydrolysis, alcoholic fermentation, distillation and dehydration of ethanol, and separation of solid residues from the vinasses.

The enzymatic hydrolysis was operated at a pH of 5, with an inlet stream containing 10% dry matter. Under the selected hydrolysis conditions, 90% of the sugar polymers were dissolved into monomers.

The sugar-containing liquor was then sent for fermentation where 90% of the sugars glucose and mannose were converted into ethanol.

The liquor was then sent for distillation, which contained a stripping step (distillation in the presence of solids) followed by a rectification step to provide an azeotropic ethanol-water mixture. The water-ethanol mixture obtained was then dehydrated over a molecular sieve to obtain the desired ethanol.

The vinasses were sent to a centrifuge to separate solid and liquid phases.

45% of the liquid phase stream obtained after liquid separation was sent to the acid cooking reactor. The cooking time was 60 minutes at 180° C. in the presence of 2% by weight of $H_2SO_4$ in solution, which represented a flow rate of 3200 kg/h.

Under these conditions, 60% of the xyloses present were converted into furfural.

This solution was then cooled and mixed with paper pulp before enzymatic hydrolysis. This resulted in the presence of 2 g/Liter of furfural in the medium, providing anti-bacterial protection during hydrolysis and fermentation.

EXAMPLE 2

A process for the production of ethanol from "Kraft" type paper pulp is considered. The pulp was obtained from hardwood pre-treated in a Kraft type papermaking process, which is an alkaline process carried out in the presence of sodium hydroxide. The lignin-depleted pulp from the Kraft process was then washed and neutralized, then introduced into the process for the conversion of cellulosic substrate into ethanol by enzymatic hydrolysis and fermentation of glucose.

The process treated 18 tonnes/hour of pulp (based on dry matter). The composition of the dry matter was as follows:

| | |
|---|---|
| Cellulose (%) | 72% |
| Xylanes (%) | 15.9% |
| Mannanes (%) | 0% |
| Others (%) | 12.1% |

The process for conversion into ethanol contained the following steps: enzymatic hydrolysis, alcoholic fermentation, distillation and dehydration of ethanol, and separation of solid residues from the vinasses.

The enzymatic hydrolysis was operated at a pH of 5, with an inlet stream containing 20% dry matter. Under the selected hydrolysis conditions, 90% of the sugar polymers were dissolved into monomers.

The sugar-containing liquor was then sent for fermentation where 90% of the glucose was converted to ethanol. The liquor was then sent for distillation, which contained a stripping step (distillation in the presence of solids) followed by a rectification step to provide an azeotropic ethanol-water mixture. The water-ethanol mixture obtained was then dehydrated over a molecular sieve to obtain the desired ethanol.

The vinasses were sent to a centrifuge to separate solid and liquid phases. 15% of the liquid phase stream obtained after liquid separation was sent to the acid cooking reactor. The cooking time was 60 minutes at 180° C. in the presence of 2% by weight of $H_2SO_4$ in solution, which represented a flow rate of 205 kg/h. Under these conditions, 60% of the xyloses present were converted into furfural. This solution was then cooled and mixed with paper pulp before enzymatic hydrolysis.

This resulted in the presence of 2 g/Liter of furfural in the medium, providing anti-bacterial protection during hydrolysis and fermentation.

EXAMPLE 3

A process for the production of ethanol from wheat straw is considered. The straw was pre-treated using an AFEX type process, which is an alkaline process carried out in the presence of ammonia. The pre-treated substrate was converted into ethanol by enzymatic hydrolysis and fermentation of glucose.

The process treated 120 tonnes/hour of straw (based on dry matter). The composition of the dry matter was as follows:

| | |
|---|---|
| Cellulose (%) | 43% |
| Xylanes (%) | 26% |
| Mannanes (%) | 0% |
| Others (%) | 31% |

The AFEX treatment does not dissolve any of the substrate and most of the chemical catalyst is recycled in the gas phase; thus, the composition of the pre-treated substrate was very similar to the incoming straw.

The process for conversion into ethanol contained the following steps: enzymatic hydrolysis, alcoholic fermentation, distillation and dehydration of ethanol, and separation of solid residues from the vinasses.

The enzymatic hydrolysis was operated at a pH of 5, with an inlet stream containing 20% dry matter. Under the selected hydrolysis conditions, 80% of the sugar polymers were dissolved into monomers.

The sugar-containing liquor was then sent for fermentation where 90% of the glucose was converted to ethanol.

The liquor was then sent for distillation, which contained a stripping step (distillation in the presence of solids) followed by a rectification step to provide an azeotropic ethanol-water mixture. The water-ethanol mixture obtained was then dehydrated over a molecular sieve to obtain the desired ethanol.

The vinasses were sent to a centrifuge to separate solid and liquid phases. 10% of the liquid phase stream obtained after liquid separation was sent to the acid cooking reactor. The cooking time was 60 minutes at 180° C. in the presence of 2% by weight of $H_2SO_4$ in solution, which represented a flow rate of 906 kg/h.

Under these conditions, 60% of the xyloses present were converted into furfural. This solution was then cooled and mixed with pretreated paper pulp before the enzymatic hydrolysis.

This resulted in the presence of 2 g/Liter of furfural in the medium, providing anti-bacterial protection during hydrolysis and fermentation.

EXAMPLE 4

A process for the production of ethanol from wheat straw is considered. The straw was pre-treated using an ARP type process, which is an alkaline process involving the percolation of an ammoniacal solution. The pre-treated substrate was converted into ethanol by SSCF (simultaneous saccharification and co-fermentation).

SSCF is a step in which enzymatic hydrolysis of sugar polymers is carried out simultaneously with fermentation of glucose and xylose (by a S. cerevisae yeast genetically modified to use C5 sugars).

The process treated 70 tonnes/hour of straw (based on dry matter). The composition of the dry matter was as follows:

| | |
|---|---|
| Cellulose (%) | 43% |
| Xylanes (%) | 26% |
| Mannanes (%) | 0% |
| Others (%) | 31% |

The ARP treatment consisted of percolating an ammoniacal solution onto the substrate, which resulted in partial delignification of the substrate as well as dissolving a portion of the hemicelluloses. The cellulose is not or is only very slightly dissolved (less than 1%). Under the selected temperature and liquid ratio conditions, 80% of the lignin was withdrawn and 51% of the hemicelluloses were dissolved.

55% of the dissolved material was withdrawn with the spent ammoniacal solution. The remaining 45% was withdrawn during successive steps for washing the pre-treated substrate.

The spent ammoniacal solution was sent to an evaporator in order to recover the reagent in the gas phase, then to a reactor where the lignin was re-condensed. A solid-liquid separation at the outlet from said reactor allowed 75% of the sugars which had been sent to be recovered. 76% of this stream was sent to the acid cooking reactor. The cooking time was 60 minutes at 180° C. in the presence of 2% by weight of $H_2SO_4$ in solution, which represented a flow rate of 874 kg/h.

Under these conditions, 60% of the xyloses present were converted into furfural. This solution was then cooled and mixed with the pre-treated straw before enzymatic hydrolysis.

The process for conversion to ethanol contained the following steps: SSCF, distillation and dehydration of ethanol, and separation of the solid residues from the vinasses.

The SSCF was operated at a pH of 4.5, with an inlet stream containing 8% of solid material. Under the selected hydrolysis and fermentation conditions, 85% of the sugar polymers was dissolved into monomers, then fermented directly into ethanol. 90% of the C6 sugars were converted, and 70% of the C5 sugars.

The liquor was then sent for distillation, which contained a stripping step (distillation in the presence of solids) followed by a rectification step to provide an azeotropic ethanol-water mixture. This mixture was then dehydrated over a molecular sieve to obtain the desired ethanol.

The vinasses were sent to a centrifuge to separate the solid and liquid phases.

Mixing the liquid derived from the acid digestion with the pre-treated straw before the SSCF step resulted in the presence of 2 g/Liter of furfural in the medium, providing antibacterial protection during the combined hydrolysis and fermentation step.

The invention claimed is:

1. A process of producing alcohol from a cellulosic or lignocellulosic substrate in which furfural is produced and which comprises at least the following steps:
    alkaline chemical pre-treating said substrate, comprising
        heating in the presence of an alkaline chemical reagent, at the end of which at least one stream comprising at least said chemical reagent and the pre-treated substrate are obtained, and
        optionally washing said pre-treated substrate, at the end of which the pre-treated washed substrate and at least one stream containing spent washing water are obtained; then
    bringing the pre-treated and optionally washed substrate to a pH in the range 4.5 to 5.5, coupled with hydrolyzing by cellulolytic and/or hemicelluloytic enzymes, by enzymatic hydrolysis, said pre-treated substrate;
    fermenting with an alcohol-producing microorganism, by alcoholic fermentation, the resultant hydrolysate at the end of which a fermentation mash is obtained comprising material in suspension and a liquid phase comprising an alcohol and vinasses; then
    separating/purifying, at the end of which purified alcohol, clarified vinasses and an insoluble residue are obtained;
    converting, by acid conversion, at least one resultant liquid obtained during one of the preceding steps and containing dissolved pentoses, whereby a portion of said pentoses are converted into furfural; and
    mixing furfural obtained during the acid conversion step with the pre-treated substrate optionally washed during the pH adjusting step, the quantity of furfural mixed in being in the range 1 to 5 g/L with respect to the total quantity of liquid in the enzymatic hydrolysis step and/or the alcoholic fermentation step.

2. The process according to claim 1, in which the alkaline chemical pre-treatment is a sodium sulphate pre-treatment, also known as the Kraft process, at the end of which paper pulp is obtained.

3. The process according to claim 1, in which the alkaline chemical pre-treatment is an ammonia fiber explosion pre-treatment or an ammonia recycle percolation pre-treatment.

4. The process according to claim 1, in which the liquid containing the dissolved pentoses during the acid conversion step is a fraction of the clarified vinasses stream obtained at the end of the separation/purification step.

5. The process according to claim 4, in which said fraction represents 5% to 75% by weight of the stream of clarified vinasses.

6. The process according to claim 4, in which the alkaline chemical pre-treatment is an ammonia fiber explosion pre-treatment or an ammonia recycle percolation pre-treatment.

7. The process according to claim 4, in which the acid conversion step is carried out at a temperature of 120° C. to 200° C., for a period of 0.5 to 3 hours, in the presence of a strong acid.

8. The process according to claim 4, in which the acid conversion step is carried out at a temperature of 130° C. to 190° C., for a period of at most 1.5 hours, in the presence of a 1% to 8% by weight sulfuric acid solution.

9. The process according to claim 4, in which the quantity of furfural mixed in is in the range of 2 to 5 g/L with respect to the total quantity of liquid in the enzymatic hydrolysis step and/or the alcoholic fermentation step.

10. The process according to claim 4, in which the quantity of furfural mixed in is 2 g/L with respect to the total quantity of liquid in the enzymatic hydrolysis step and/or the alcoholic fermentation step.

11. The process according to claim 1, in which the liquid containing the dissolved pentoses during the acid conversion step is a fraction of the stream containing at least the chemical reagent and the pre-treated substrate obtained after the pre-treatment step.

12. The process according to claim 11, in which said fraction represents 10% to 100% by weight of said stream.

13. A process according to claim 1, in which the liquid containing the dissolved pentoses during the acid conversion step is a fraction of the stream containing the spent washing water, obtained after the pre-treatment step.

14. A process according to claim 13, in which said fraction represents 10% to 100% by weight of said stream.

15. A process according to claim 1, in which the acid conversion step is carried out at a temperature of 120° C. to 200° C., for a period of 0.5 to 3 hours, in the presence of a strong acid.

16. A process according to claim 1, in which the acid conversion step is carried out at a temperature of 130° C. to 190° C., for a period of at most 1.5 hours, in the presence of a 1% to 8% by weight sulphuric acid solution.

17. The process according to claim 1, in which the acid conversion step is carried out at a temperature of 120° C. to 200° C., for a period of 0.5 to 3 hours, in the presence of sulfuric acid or phosphoric acid.

18. The process according to claim 1, in which the acid conversion step is carried out at a temperature of 130° C. to 190° C., for a period of 0.5 to 1.5 hours, in the presence of a 1% to 8% by weight sulfuric acid solution.

19. The process according to claim 1, in which the quantity of furfural mixed in is in the range of 2 to 5 g/L with respect to the total quantity of liquid in the enzymatic hydrolysis step and/or the alcoholic fermentation step.

20. The process according to claim 1, in which the quantity of furfural mixed in is 2 g/L with respect to the total quantity of liquid in the enzymatic hydrolysis step and/or the alcoholic fermentation step.

* * * * *